United States Patent
Zscheeg

(10) Patent No.: US 6,911,041 B1
(45) Date of Patent: Jun. 28, 2005

(54) EXPANDED STENT AND A METHOD FOR PRODUCING SAME

(75) Inventor: Harry Zscheeg, Karlsruhe (DE)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/530,003
(22) PCT Filed: Oct. 22, 1998
(86) PCT No.: PCT/EP98/06717
§ 371 (c)(1), (2), (4) Date: Apr. 21, 2000
(87) PCT Pub. No.: WO99/21509
PCT Pub. Date: May 6, 1999

(30) Foreign Application Priority Data

Oct. 23, 1997 (DE) .......................................... 197 46 882

(51) Int. Cl.[7] ................................................. A61F 2/06
(52) U.S. Cl. ...................................... 623/1.15; 623/1.2
(58) Field of Search ................................. 623/1.36, 1.1, 623/1.11, 1.15, 1.18, 1.19, 1.22; 219/121.67, 121.68, 121.6; 606/194

(56) References Cited

U.S. PATENT DOCUMENTS

| 5,514,154 A | 5/1996 | Lau et al. | |
|---|---|---|---|
| 5,707,386 A | * 1/1998 | Schnepp-Pesch et al. | ... 606/194 |
| 5,716,393 A | 2/1998 | Lindenberg et al. | |
| 5,913,897 A | * 6/1999 | Corso, Jr. et al. | ............ 623/1.1 |
| 5,972,027 A | * 10/1999 | Johnson | ...................... 623/1.1 |
| 6,270,524 B1 | * 8/2001 | Kim | ......................... 623/1.15 |

FOREIGN PATENT DOCUMENTS

| CA | 2155527 | 8/1994 | |
|---|---|---|---|
| EP | 0688545 | 12/1995 | |
| EP | 0712614 | 5/1996 | |
| EP | 792627 | * 9/1997 | ................. 623/1.1 |
| WO | WO9618359 | 6/1996 | |

* cited by examiner

Primary Examiner—Julian W. Woo

(57) ABSTRACT

An expandable stent for insertion into a body lumen has a generally cylindrical lattice structure formed from wall segments that intersect and with some of the intersections being interrupted to enhance the flexibility of the stent. The wall segments associated with the interrupted portions are formed to have an outward flare such that when the stent is in a curved configuration, the wall segments will not project radially inwardly into the stent lumen, thereby avoiding obstruction to flow through the lumen.

14 Claims, 4 Drawing Sheets

EXPANDED STENT AND A METHOD FOR PRODUCING SAME

TECHNICAL FIELD

Figure 1:
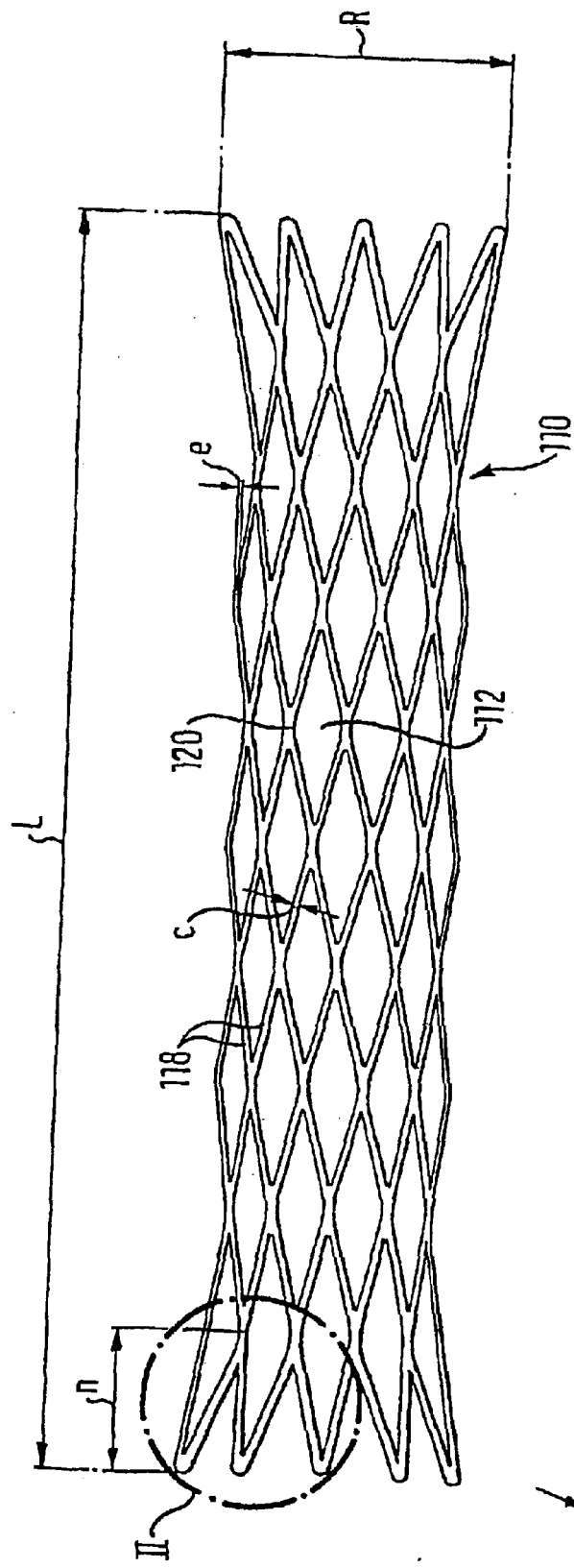

The present invention concerns expandable stents for insertion into tubular anatomical structures, such as the bile duct, liver, arteries, esophagus, trachea or the like, as well as a method for the production of such a stent. Below, such tubular anatomical structures will be described e.g. as vessels or bodily vessels.

STATE OF THE ART

Stents of this class may consist of plastic or of an inert metal such as, for example, steel or metal alloys. Typical fields of use are the expansion of a urethra in the prostate zone in the case of benign prostate hyperplasia (BPH) or in pathologically constricted blood vessels for the expansion and keeping open of these vessels. They have a lattice structure, which consists of wall segments and of apertures which are formed between these wall segments. This structure makes it possible for the stent to be enclosed by growth of the tissue of the vessel in which it is inserted. It is known to form stents in the manner of a spirally wound helix; they may consist of woven or knitted wire or plastic material. Stents of this class can on the one hand be permanently plastically deformable (balloon expandable stents), but on the other hand they can be elastic or superelastic (self-expanding stents) or have shape memory properties (also self-expanding stents), as are present, for example, in certain nickel-titanium alloys (Nitinol®).

It is frequently desirable to use stents in accordance with this class in curvatures of vessels. Such vessel curvatures may have very small radii of curvature. For this field of application, highly flexible stents have been developed. Thus, for example, DE 43 03 181 A1 discloses a stent which can be implanted and which has higher flexibility and bending capacity as well as better stability when being bent than the stents which were previously known. These properties are achieved by providing the stent with a plurality of circumferentially extending meandering tracks that are arranged one behind the other in the axial direction. These meandering tracks are connected with each other by connecting sections; however, between each connecting sections facing each other, there are in the peripheral direction at least two connecting sections which are not connected with each other but which face each other. This resolution of a firm lattice structure achieves the desired strength properties. However, when using this known stent in very narrowly curved vessel zones, it may happen that the edges of the connecting sections which are not connected with each other project into the internal lumen of the tubular structure in such manner that the usable cross-sectional area of the stent is reduced.

In addition, stents are known in which, so as to improve the anchorage of the stent in the surrounding vascular tissue, the end zones of the stent are thickened so that the stent does not have a uniform external diameter over its entire length. The thickened ends which project outwardly are grown around by the vascular tissue and prevent a change in the position of the stent in its axial direction. Such an embodiment is known, for example, from EP 0 778 011 A2.

In order to prevent such a change of position by other means, it has also been suggested in WO 86/02211 that a lattice structure of a stent should in addition be provided with projecting barbs in the direction of the vascular tissue. However, the basic lattice structure of this stent is not altered thereby.

SUMMARY OF THE INVENTION

It is the object of the present invention to make available an expandable stent, which meets the maximal demands for positional stability and which is suitable for application sectors, in which it is exposed to strong curvatures. In addition, it is the object of the present invention to make available a production process for a stent achieving these objects.

These objects are advantageously attained by an expandable stent of the present invention. Advantageous embodiments and/or further developments of the expandable stent are also provided herewith.

Thus, an expandable stent in accordance with the invention comprises an elastic tubular lattice structure which has a first end zone, a second end zone, a longitudinal direction and a radial direction. This lattice structure defines an outer diameter and an inner lumen. It is formed by wall segments, these wall segments branching off at intersections. In addition, the lattice structure is interrupted in at least some of these intersections, whereby the flexibility of the stent is increased. The expandable stent in accordance with the invention is characterized in that at least at the interrupted intersections, the wall segments are expanded in the radial direction of the stent. Consequently, this expansion is directed towards the vascular tissue which surrounds the stent, the interrupted intersections being located between the first end zone and the second end zone of the lattice structure. The expansion in the radial direction has the effect that even in the case of extreme curvature of the stent along the longitudinal direction, the inner lumen of the vessel is not reduced because the wall segments project into the inner lumen at the interrupted intersections. The solution in accordance with the invention provides a plurality of advantages. Thus it is possible on the one hand to expand and thereby to implant the inventive stent by means of a balloon catheter, irrespective of the curvature of the location in the body which is to be treated, or to treat with balloon catheters the vascular tissue at that location where stents have already been implanted, and on the other hand to design the stent as a self-expanding stent. In addition, a local reduction of the inner lumen could lead to uncontrollable vascular system vortices in the liquid which flows through the stent and thereby could lead to new occlusion reactions. This is also prevented by the solution in accordance with the invention. At the same time, due to the expansion of the wall segments in the radial direction of the stent at the interrupted intersections, the anchorage of the stent in the surrounding vascular tissue is improved, so that the stent cannot change its position, after it has been implanted. It will be understood that depending on the production process which is selected for the stent, the wall segments can also be expanded at the uninterrupted intersections.

In accordance with an advantageous further development, in addition, the wall segments in the first and/or second end zone are expanded in the radial direction, whereby the anchorage is supported and terminations of the stent are achieved which are directed to the exterior. Consequently, conical and/or bulging forms of the stent are possible. Even flow transitions without Karman vortex streets are ensured. In order to also design the expansion of the wall segments to be even and optimally with respect to the flow conditions, the expansion is formed by an arcuate curvature of these wall segments along the longitudinal direction. Within the scope of the present invention, it is also provided that the expansion can be generated e.g. by bends, which however are less preferred than the arcuate curvatures.

Advantageously the stent is further developed such that the wall segments are interrupted in regular distribution over the stent, substantially at two thirds of all the intersections. This distribution is regular both in the peripheral direction as well as in the axial direction of the stent and the exact pattern of the distribution depends on the form which was selected for the lattice structure. It has been found that an interruption of substantially two thirds of all the intersections is a good compromise between high strength for the stent on the one hand and good flexibility and stability upon deformation of the stent on the other. The flexibility which is thus achieved can also be altered as desired depending on the medical indication, by having a correspondingly different number of intersections be interrupted.

As was mentioned above, the lattice structure has apertures. In the case of collateral arterial branches, so as to improve the guarantee of further regional supply of the vessels until a re-growth of intima takes place, these apertures advantageously have in the expanded state of the stent an aperture width of maximally 9 mm.

In order to keep the danger of re-occlusion of the vascular tissue at the point of implant as low as possible, the stent has to have a certain restoring force. For this restoring force it is especially favorable when the wall segments have a width between 0.12 mm and 0.17 mm. Width is to be understood as the minimal extension of the wall segments from the aperture of the lattice structure which is adjacent to this wall segment on one side to the adjacent aperture of the lattice structure on the opposite side, substantially in the peripheral direction of the stent.

In order to further develop with advantages the favorable properties of a no-profile stent or of a low-profile stent, the lattice structure in the radial direction has substantially a wall thickness of between 0.2 mm and 0.3 mm. Because this wall thickness may slightly fluctuate in the course of the longitudinal direction of the stent, depending on the production process, the information above is understood as a characteristic wall thickness. In accordance with another advantageous design of the stent in accordance with the invention, it consists of a metallic material which has shape memory. For further advantage, this material with its shape memory effect consists of a nickel-titanium alloy. The alloy moieties, which are especially advantageous in accordance with a preferred range of the alloy moieties, make it possible to design the stent to react to temperature so that it can be inserted into the body in the non-expanded state, expands due to the body temperature when positioned to the required extent and is independently implanted at the position which it is desired to treat.

The production process for a stent in accordance with the invention provides for the provision of a tubular element with an external diameter, an inner lumen, a first end zone and a second end zone. Further, for forming a lattice structure, the tubular element is slotted. By slotting, the generation of slot-type apertures by means of mechanical (e.g. punching), electromagnetic or electrical (e.g. laser cutting or electrical discharge machining) or chemical production processes (e.g. by etching) is to be understood. This lattice structure resulting from the slotting is formed by wall segments which branch off at intersections. In a further step, at least some of the intersections are interrupted at selected positions, whereby the flexibility of the stent is increased. Depending on the chosen method of production, it is advantageous under certain circumstances to carry out the steps of slotting and of interruption at the same time. In addition, at the interrupted intersections the wall segments are expanded in the radial direction such that upon curvature of the stent along the longitudinal direction, a reduction of the inner lumen by the wall segments at the interrupted intersections is prevented. Here as well it can be seen that it may be advantageous to expand the wall segments at the non-interrupted intersections as well.

In addition, it is provided in accordance with the invention that the step of expanding also includes expanding the wall segments in the radial direction at the first and second end zones.

It has been found to be especially economical in terms of the process to carry out the inventive process steps in the sequence provided herewith.

In accordance with an advantageous further development of the process in accordance with the invention, it is further provided that after the slotting of the tubular element and before interrupting the intersections, a step is included in which the structure of the metal lattice of the stent is influenced in order to program the shape memory effect.

In order to influence favorably the flow conditions in and around the stent, it is further provided in accordance with the invention that the production process is concluded by a step in which the stent is polished. Due to the polishing, the surface becomes extremely smooth and possibly extant or resultant scratches, burrs or irregularities in the surface in general are removed.

In addition, it is advantageously provided in accordance with the invention that the step of expanding comprises a plurality of partial steps, which ideally are carried out in the stated sequence. Consequently on the one hand the stent is positioned on a mandrel, in which the shape of the mandrel is designed as the counterpart to the expanded shape of the stent. This positive-negative shape relationship is used to provide the stent with the form of the mandrel. In this connection, the dimensions of the mandrel substantially correspond to the dimensions of the stent in the expanded state. After the stent has been placed on the mandrel, the stent or both the stent and the mandrel are heated. Subsequently, the stent and optionally the mandrel are cooled off and the cooled stent is removed from the mandrel. The heating and cooling steps can advantageously be carried out by a mandrel which can be heated as well as cooled. On the other hand, it is conceivable that to heat the stent from the exterior. It is ensured that the stent as a whole, together with the expanded wall segments, shows a temperature reactive behavior.

It is also possible to generate the desired shape of the stent from the exterior, e.g. by providing an external mold element radially outside the stent as a counter-mold, which corresponds in its contour to the expanded shape of the stent. It is especially desirable that the stent should be shaped in such a way that a mandrel is used in combination with such a molding element.

In the manner already described, it is advantageous for the stent to consist of a metallic material. In accordance with a preferred embodiment of the inventive process, this material has a threshold temperature at which dislocations in the material of the stent re-direct themselves. In accordance with the invention, the stent is heated in the partial step of heating to a temperature above this dislocation threshold temperature, and in the step of cooling it is cooled to a temperature below this dislocation threshold temperature. Thereby it becomes possible to adjust the temperature reactive properties of the stent exactly to the circumstances with respect to e.g. the human body temperature. The shape memory effect or shape memory capacity is consequently programmed with its reaction parameters.

SHORT DESCRIPTION OF THE DRAWINGS

Figure 2:
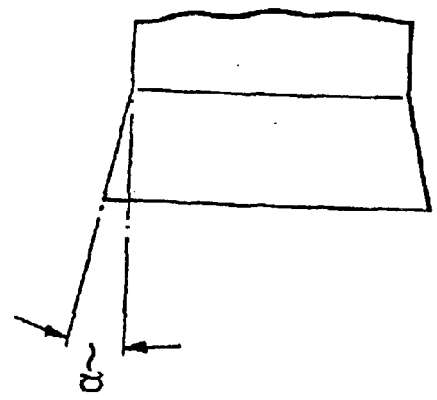
Figure 3:
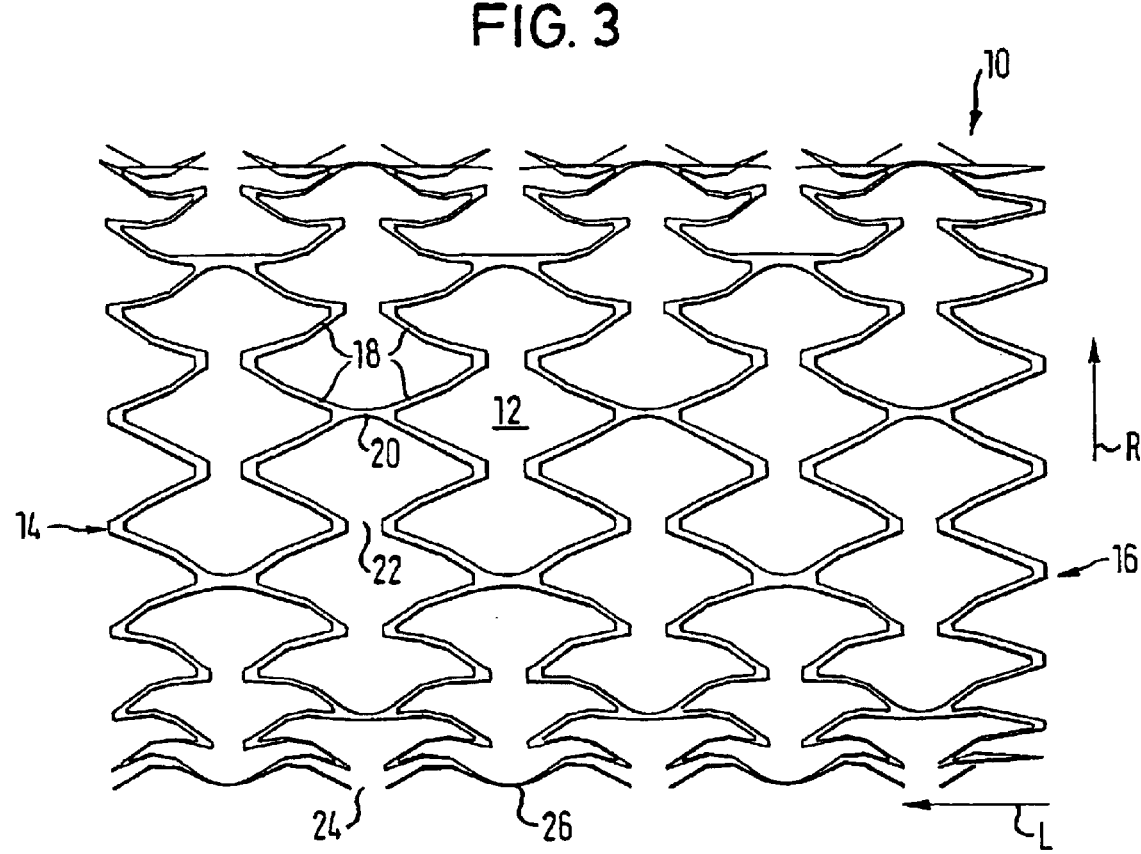
Figure 4:
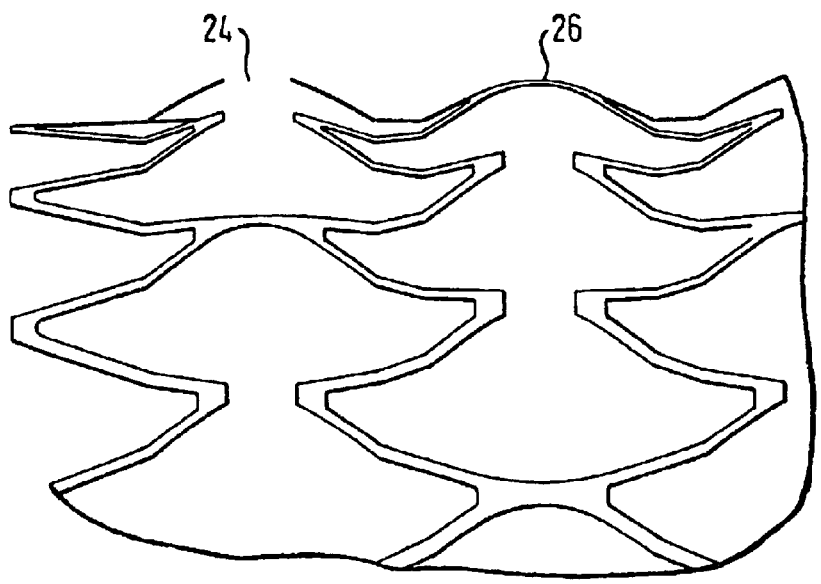
Figure 5:
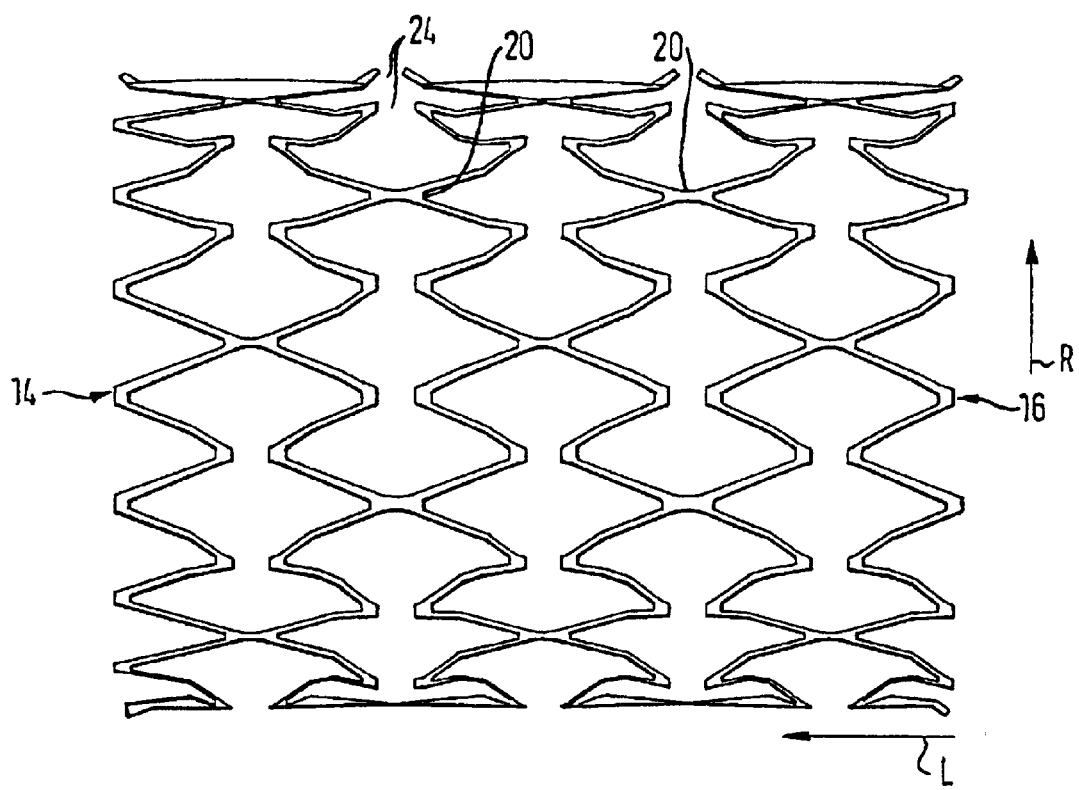
Figure 6:
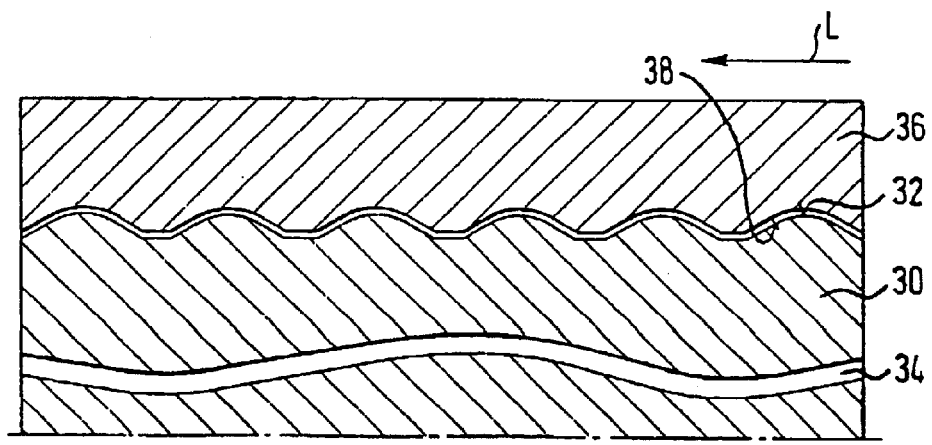
Figure 7:
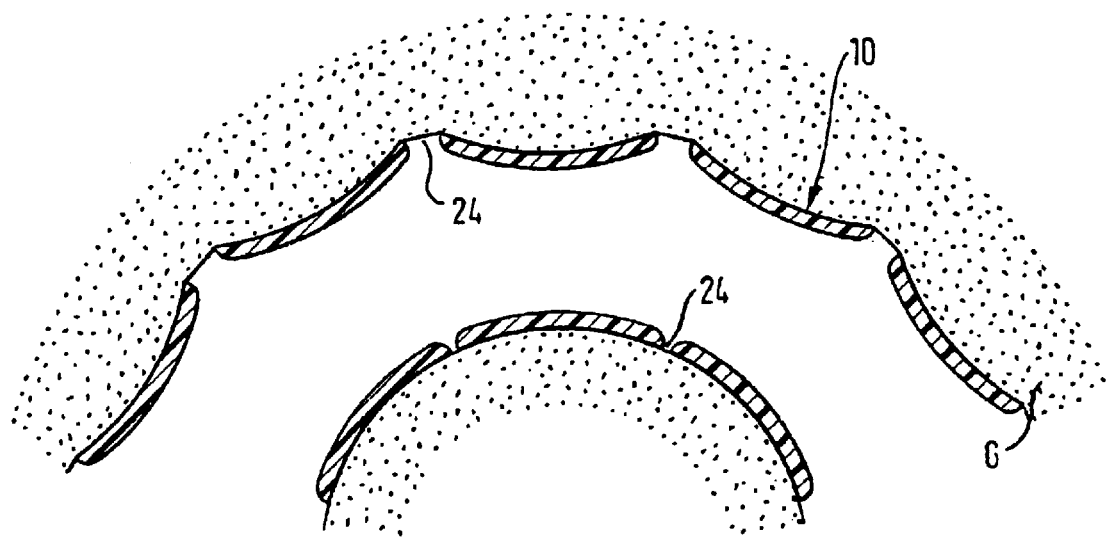

For further explanation and for better understanding of the invention, examples of the embodiments of the invention will be described below with reference to the enclosed drawings. It is shown in:

FIG. 1 a stent in accordance with the prior art, in which the characteristic magnitudes of a stent in accordance with this class are characterized in the Figure for use given a certain medical indication;

FIG. 2 a detail of a conventional stent in accordance with FIG. 1, which is marked there as II;

FIG. 3 a side view of a stent in accordance with the invention in a first embodiment;

FIG. 4 an enlarged cut-out from FIG. 3;

FIG. 5 a side view of a stent in accordance with the invention in a second embodiment;

FIG. 6 a device which is used in accordance with a preferred embodiment in the process in accordance with the invention; and FIG. 7 schematically a stent in accordance with the invention in the inserted state, in which the stent is inserted at the point of a sharp curvature.

DESCRIPTION OF EXAMPLES OF EMBODIMENTS

FIG. 1 shows a side view of a conventional stent of this class. The conventional dimensional conditions of the stent for use in the carotid can be inferred from the side view. Such stents, inter alia, have a longitudinal direction L and a radial direction R and in addition they define an inner lumen.

For the stent in accordance with the invention, which is shown in FIGS. 3 to 5, certain dimensions are especially advantageous for the medical indication of use in the carotid. To simplify the illustration, those details, the dimensions of which are important to the stent in accordance with the invention, are indicated at corresponding details of the stent in accordance with the prior art shown in FIG. 1.

From FIG. 1 it can be seen that the conventional stent 110 consists of a lattice structure 112. This lattice structure is formed by various wall segments 118, which branch off at the intersections 120. The length of the wall segments from intersection to intersection is marked as n and the width in the peripheral direction is marked as c. The thickness of the wall in the radial direction is marked as e.

From FIG. 2 it can be discerned at which angle α the wall segments 118 deviate at the intersections 120 from the longitudinal direction L of the stent. The length n of the wall segments from intersection to intersection in combination with the angle a defines the maximal width of the aperture, which in the illustrated exemplary embodiment is formed in the peripheral direction between the intersections.

FIG. 3 shows a first example of an embodiment of a stent 10 in accordance with the invention. This inventive stent has a radial direction R and a longitudinal direction L and in addition a first end zone 14 and a second end zone 16. The typical radial and/or longitudinal dimensions of the stent 10 differ from those of the conventional stent 110 which is shown in FIG. 1. These dimensions are chosen depending on the medical indication. The stent 10 in accordance with the invention (FIG. 3) is formed by a lattice structure 12. This lattice structure has a plurality of wall segments 18, which branch off at intersections. Of these intersections, some (22) are interrupted, but others (20) are not. The interruption of some intersections 22 in a regular distribution over the stent 10 makes it possible to increase the flexibility of the entire stent. Depending on the medical indication, a corresponding plurality of intersections is interrupted in regular distribution over the stent. It is especially advantageous when the intersections 20 which are not interrupted are not directly adjacent.

Advantageously, for the inventive stent for the described medical indication, the wall segments forming the lattice structure have a segment length n (see FIG. 1) of 4 mm from intersection to intersection. The angle α (which is also shown in FIG. 1) at which the wall segments deviate at the intersections from the longitudinal direction L of the stent, amounts advantageously to 15°, the width c of the wall segments preferably being 0.132 mm and the thickness of the wall e of the stent amounting preferably to 0.2 mm.

The stent in accordance with the invention can be produced as to its shape by a suitable molding tool. This production will be explained in still more detail later with reference to FIG. 6.

In accordance with the exemplary embodiment shown in FIGS. 3 and 4, expanded intersections 24 are provided at all the interrupted intersections 22 as well as expanded intersections 26 are provided at the non-interrupted intersections 20. In addition, it can be inferred from FIG. 3 that the stent in accordance with the invention is designed to be asymmetrical. This asymmetry refers to the fact that the first end zone 14 of the stent is expanded in a comparable way, like the expanded interrupted intersections 24 and the expanded non-interrupted intersections 26. By contrast, the second end zone 16 is not expanded. Such asymmetrical configurations can be advantageous depending on the field of application. In this context it should be noted that in accordance with the present invention, although the figures show substantially cylindrical examples of embodiments, conical, bulging embodiments or examples of embodiments which are divided in the form of a branch can be employed.

FIG. 4 shows an enlarged detailed view of FIG. 3. From the figure it can clearly be inferred how in accordance with the preferred embodiment of the invention, expanded interrupted intersections 24 and expanded non-interrupted intersections 26 are arranged so that in the peripheral direction around the stent, continuing elevations and recesses are formed. In the longitudinal direction of the stent, a cyclically repeating arc form is produced. As can be inferred from the figure, this arc form is designed in such a way that the ends of the wall segments at the expanded interrupted intersections extend again substantially in parallel with the longitudinal direction L of the stent. Although the arcuate expansion of the wall segments is preferred at the interrupted and uninterrupted intersections, expansions of other forms are also conceivable. For example, the wall segments at the interrupted intersections do not have to be expanded in an arcuate manner, but they can also deviate to the exterior at an angle in polygon shape, so that the expanded parts of the wall segments are straight.

FIG. 5 reproduces a second example of an embodiment of the present invention. In accordance with this second example of an embodiment, the stent also has a radial direction R and a longitudinal extension L. One difference from the stent in accordance with the invention in accordance with the first embodiment is that the stent which is shown in FIG. 5 is not expanded at its uninterrupted intersections 20, i.e. that there it extends in accordance with its original shape, which is substantially cylindrical. On the other hand, the interrupted intersections are designed in the form of expanded interrupted intersections 24. A further difference from the first embodiment is that the stent which is shown in FIG. 5 is designed to be symmetrical, i.e. that it is expanded both in its first end zone 14 as well as in its second end zone 16. By analogy with the production of the embodiment which was first described, this embodiment can also be generated by a suitably shaped molding tool.

In FIG. 6 a tool is shown which is suitable for the production of a stent in accordance with the invention. The tool mainly consists of a core 30 and an outer mold 36. The core 30 is in general designed to be substantially cylindrical and it has on its exterior a molding surface 32. This core molding surface 32, as can be seen from the cross-sectional view in FIG. 6, is designed in the direction of the longitudinal extension L of the stent to be approximately sinusoidal. This sinusoidal shape corresponds to a possible desired course of the wall segments and of the stent, so that the expanded interrupted intersections 24 and possibly the expanded uninterrupted intersections 26 are arcuate, namely they are expanded in the shape of the sine curve. The external mold 36 also has a molding surface 38. This external molding surface 38 is designed such that it forms a counter-part to the core molding surface 32. Preferably the outer mold 36 is designed so it can be separated, so that it can be placed in a suitable manner on the core 30.

As also follows from FIG. 6, the core 30 can be provided with cooling or heating channels 34, of which only one is schematically shown in the Figure. These heating channels can extend in the longitudinal direction of core 30 or helically in the peripheral proximity of the core. It is also conceivable that the core 30 should be heated and cooled from the exterior, as well as in certain circumstances the outer mold 36 and the stent which is to be expanded. If cooling and/or heating channels 34 are to be used, for example oil is a suitable medium for heating or cooling the core. During the process of expansion, the stent comes to rest between the core mold surface 32 and the outer mold surface 38.

In the following, the production of the stent in accordance with the invention will be explained.

In general the starting point for a preferred production process for a stent in accordance with the invention is a tubular element. This tubular element has an outer diameter and defines an inner lumen. The dimensions of the inner lumen correspond to those of the outer diameter reduced by the wall thickness of the tubular element. In the longitudinal direction L of the stent, it extends from a first end zone 14 to a second end zone 16. Preferably, the tubular element consists of Nitinol®, Nitinol being an alloy which consists of the alloy components nickel and titanium with the following mass moieties: 54.5 to 57 mass percent nickel and 43 to 45.5 mass percent titanium. The nickel and titanium contents should result in their totality in 100 mass percent, with the exception of some impurities which are possibly present. Nitinol®, on the basis of its very strongly marked shape memory effect, has good physical and mechanical properties in use, it is corrosion inert and the biological compatibility has been found to be specially suitable for stomatology and implantology.

For radiological stents, stents without multi-layer intersections of the wall segments are preferred. A thin-walled structure guarantees that no vascular lining results which restricts the lumen. In order to produce the lattice structure typical for the shown stents from the tubular element, this tubular element is slotted in a further production step to form a lattice structure. What is meant by slotting in the sense of the present invention is the generation of apertures similar to slots. Generally, slotting takes place in the non-expanded state and the slot-like apertures are preferably produced by laser cutting. As has already been mentioned, however, other processes are also conceivable, including chemical, mechanical, electro-magnetic or electrical processes. By way of slotting, slot-like apertures are formed which are surrounded by individual wall segments. In those zones in which two slot-like apertures are adjacent, the wall segments branch off at intersections.

In order to provide the stent with the desired flexibility, preferably when generating the slot-type apertures, a flexibility slotting is carried out at the same time. In this step, some of the intersections are interrupted by slotting. Depending on the strength properties desired for the resultant structure, different numbers of intersections are interrupted. If it is so desired that the flexibility of the stent is homogeneous in the totality of the stent region, the interrupted intersections must be regularly distributed. If locally higher flexibility is desirable, in the zones of higher flexibility more intersections can be interrupted than in the zones of lower flexibility. It has been found to be an advantage when two thirds of all the intersections are interrupted, and that the pattern of this interruption should be designed to be regular, so that there are neither in the longitudinal direction nor in the peripheral direction of the stent adjacent uninterrupted intersections.

In a particularly preferred use of the stent in accordance with the invention, it is self-expanding, and in fact depending on its ambient temperature. This temperature reactive expansion, in the case of a metallic stent, takes place due to the transformation of the crystalline metal lattice structure from a martensite structure into an austenitic structure. Preferably, the formation of the austenitic structure is concluded just below the body temperature, i.e. at about 35° C. In addition to the properties directly connected with the crystal lattice structure, such as, for example, capacity for magnetization or the like, the strength of the stent is also altered favorably. On attaining the so-called austenitic plateau, the stent has a greater strength against deformation. This programming of the shape memory effect, so that the stent as a result is temperature reactive, takes place in a heat treatment step. In this step, the stent is heated for an adequate time to a temperature at which dislocations of the crystal lattice are released. This temperature is described here as the "dislocation threshold temperature". The level of the temperature depends on the materials which are chosen.

Advantageously, this programming of the shape memory effect can be combined with an expansion of the wall segments at the desired positions. To do this, the stent is preferably positioned before heating on a core 30, which is shown in the lower part of FIG. 6. This core has on its exterior a core mold surface 32, which corresponds in its contour to the desired end contour of the stent. In order to facilitate the deformation of the stent, it is an advantage to also provide an outer mold 36. This outer mold 36 also has a mold surface 38, the stent which is to be treated being located between the core mold surface 32 and the outer mold surface 38, when the outer mold 36 is placed on the mold 30. As already mentioned, the outer mold 36 is preferably divided so that it can be positioned on the core with stent, possibly with gradually increasing force. The elevations which can be inferred from the drawing and are provided in the radial direction of the core on the core mold surface 32 can run around the core, which has a substantially cylindrical form.

Then the core with the stent and in certain circumstances the outer mold is brought by suitable means to the above-mentioned temperature in order to program the shape memory effect.

After the corresponding cooling, the stent can be removed from the outer mold and core by removing the outer mold and drawing the stent off the core. The elasticity and the flexibility of the stent facilitate its removal from the core 30, without causing damage to the core and, above all, to the stent.

In order to overcome possible surface irregularities, such as scratches, burrs or the like which may be present already or may result from the production process, it is provided that the stent is polished, before it is inserted into, preferably drawn into, an application system which corresponds to the medical indication. Such an application system can, for example, be one by which a percutaneous transluminal angioplasia can be carried out and it is used as an example for a system in accordance with the Seldinger technique for the retrograde or antegrade catheterization of bodily vessels.

With reference to FIG. 7, the effect of the stent in accordance with the invention will be described below.

In FIG. 7 it is schematically shown how the stent 10 in accordance with the invention behaves in a curved vessel G. The stent is shown in a phase in which it has contacted the wall of a vessel G after the expansion process, or has been brought into contact therewith. It is clear how the expanded interrupted intersections 24 smoothly adapt in their course and in their shape to the wall of the vessel on the interior of the curvature. In addition, on the outer side of the curvature, the wall segments at the interrupted intersections 24 do not project into the inner lumen of the catheter, but they are oriented towards the surrounding vascular tissue. They project far enough into the vascular tissue so that the wall segments contact gently between the intersections the wall of the vessel.

The expansion of the stent has the effect that the inner lumen of the vessel, even in the zones of strong curvature, in particular on the internal side of the curvature is not reduced due to the fact that the wall segments project into the lumen in addition, a change in the position of the stent is made more difficult, because the wall segments which point in the direction of the vascular tissue, in particular on the outer side of the curvature, become anchored in the vascular tissue.

What is claimed is:

1. A self expandable stent comprising:

an elastic tubular lattice structure having a first end zone, a second end zone, a longitudinal direction and a radial direction, the lattice structure defining an outer diameter and an inner lumen and being formed by wall segments, which wall segments branch off at intersections, the stent being elastically expandable from a compressed, reduced diameter delivery configuration toward a relaxed, resiliently expanded configuration the lattice structure being interrupted at least at some of the intersections so as to increase the flexibility of the stent, the wall segments at least at the interrupted intersections, being pre-formed to have a relaxed, undeformed and resiliently expanded state in which they project radially outward such that, upon curvature of the expanded stent along the longitudinal direction, a reduction of the inner lumen due to the wall segments at the interrupted intersections is prevented, the stent, including the radially expandable wall segments at the interrupted intersections, being compressible to a reduced diameter containable in a delivery device such that the stent, including the radially projectable wall segments, are resiliently contained such that upon release from the delivery device, the stent will resiliently self-expand to its expanded state and the wall segments will radially self-expand to their outward projecting configuration.

2. A stent in accordance with claim 1, wherein the expansion of the wall segments is formed by an arcuate curvature of these wall segments along the longitudinal direction.

3. A stent in accordance with claim 1, wherein the wall segments are interrupted in regular distribution over the stent at substantially two thirds of all the intersections.

4. A stent in accordance with claim 1, wherein the lattice structure has apertures having an aperture width of maximally 9 mm when the stent is expanded.

5. A stent in accordance with claim 1, wherein the wall segments have a width between 0.12 mm and 0.17 mm.

6. A stent in accordance with claim 1, wherein the lattice structure has substantially a wall thickness of between 0.2 mm and 0.3 mm.

7. A stent in accordance with at least one of claims 1 and 2-6, wherein the stent consists of a metallic material.

8. A stent in accordance with claim 7, wherein the metallic material consists of a shape memory alloy.

9. A stent in accordance with claim 8, wherein the metallic material consists of an alloy which contains nickel and titanium.

10. A stent in accordance with claim 9, wherein the alloy of the stent has the following alloy moieties:

nickel: 54.5 to 57 mass percent, titanium: 43 to 45.5 mass percent.

11. A combination of an expandable stent and a stent delivery system comprising:

a stent as defined in claim 1 and a stent delivery device for delivering the stent.

12. A combination in accordance with claim 11, wherein the delivery system contains a balloon dilation catheter.

13. A combination in accordance with claim 11, wherein the delivery system is a system in accordance with the Seldinger technique for catheterization of bodily vessels.

14. A combination in accordance with claim 11, wherein the stent consists of a metallic material made from a shape memory alloy having the following alloy moieties:

nickel: 54.5 to 57 mass percent, titanium: 43 to 45.5 mass percent.

* * * * *